United States Patent
Hammons et al.

[11] Patent Number: 6,085,026
[45] Date of Patent: Jul. 4, 2000

[54] ELECTRICALLY HEATED VAPOR DISPENSING APPARATUS

[75] Inventors: Randall Lee Hammons, Sussex; Manhar Patel, Saddle Brook, both of N.J.

[73] Assignee: Reckitt Benckiser Inc., Wayne, N.J.

[21] Appl. No.: 08/665,856

[22] Filed: Jun. 19, 1996

[30] Foreign Application Priority Data

Jun. 22, 1995 [GB] United Kingdom .................... 9512708

[51] Int. Cl.⁷ .............................. A61M 16/00; H05B 3/44
[52] U.S. Cl. ............................................ 392/390; 219/544
[58] Field of Search ................................... 392/386, 387, 392/390; 219/541, 542, 543, 544; 338/22 R, 243, 248, 273, 276

[56] References Cited

U.S. PATENT DOCUMENTS

| | | | |
|---|---|---|---|
| 2,942,090 | 6/1960 | Diehl | 392/390 |
| 3,581,266 | 5/1971 | Weyenberg | 338/253 |
| 4,037,082 | 7/1977 | Tamada et al. | 219/451 |
| 4,804,821 | 2/1989 | Glucksman | 392/390 |
| 4,849,606 | 7/1989 | Martens, III et al. | 219/271 |
| 4,853,517 | 8/1989 | Bowen et al. | 392/390 |
| 5,213,523 | 5/1993 | Hygema et al. | 439/620 |
| 5,402,517 | 3/1995 | Gillett et al. | 392/386 |
| 5,521,357 | 5/1996 | Lock et al. | 392/390 |
| 5,556,192 | 9/1996 | Wang | 392/390 |
| 5,574,821 | 11/1996 | Babasade | 392/392 |
| 5,647,052 | 7/1997 | Patel et al. | 392/393 |

FOREIGN PATENT DOCUMENTS

| | | |
|---|---|---|
| 0195967 A2 | 10/1986 | European Pat. Off. . |
| 0498278 A1 | 8/1992 | European Pat. Off. . |
| 2117639 | 10/1983 | United Kingdom . |
| 2192337 | 1/1988 | United Kingdom . |
| WO 94/15650 A1 | 7/1994 | WIPO . |

*Primary Examiner*—Sang Paik
*Attorney, Agent, or Firm*—Fish & Richardson P.C.

[57] ABSTRACT

An electrically heated apparatus for dispensing fragrancing materials and other volatile substances to an enclosed volume such as the interior of a room which includes a base having a base portion which is generally planar in structure having a top surface, and a bottom surface from which extends perpendicularly two (or more) suitably dimensioned electrical plugs. The base portion further includes incorporated within its construction a heating means which, when the electrical plugs are connected to a suitable electrical source, said heating means is energized, resulting in the heating of the base portion. Further, the base portion of the invention includes a radiator means. The apparatus further includes a volatile substance container which contains a quantity of a volatile substance such as a fragrance or perfume, a disinfecting composition, or an insecticide. The radiator means provides a surprisingly uniform temperature across the top surface of the base portion.

15 Claims, 8 Drawing Sheets

ELECTRICALLY HEATED VAPOR DISPENSING APPARATUS

The present invention relates to electrically heated vapor dispensing apparatus of the type commonly used for dispensing fragrancing materials and other volatile substances to an enclosed volume such as the interior of a room.

Electrically heated vapor dispensing apparatus of different types are known to the art. For example, from UK patent application No. 2117639 to Brookes, therein is described an air freshening device which includes an electrical plug having a base, a lid, and a heat barrier plate interposed therebetween. The device further includes an impregnated paper tablet and vertical air flow passages. The lid further includes a heating element as well as a light emitting diode indicating operation of the heating element. In use, the impregnated paper tablet is heated by the heating element, thus volatilizing the material contained therein, generally a perfume, which then passes through the vertical air flow passages to the surrounding ambient environment. A further device is one which is disclosed in EP Appn. 92101394.2 to Lempidakis wherein is also provided an electrically heated air freshening device having means for controlling natural airflow through the device and thereby release of a volatile substance.

Therein is also described in U.S. Pat. No. 5,402,517 to Gillett an apparatus for emitting a volatile chemical agent, with means for adjusting the heating of a volatilizable material.

There is also known a tamper resistant container for use in conjunction with an electrically heated vapor dispensing apparatus from U.S. Pat. No. 4,849,606 to Martens III. The Martens' device includes a tamper resistant package which includes a container having a free-standing rib extending from the bottom in an upward direction. The open side of the container is covered with a vapor permeable membrane, and the container itself contains a quantity of a fragrance material in a carrier gel. The technical advantage of such container is recited as a reduced propensity for the damage of the membrane during the handling and insertion of said container into an electrically heated vapor dispensing apparatus which is dimensioned for receiving the container.

While these recited apparatus are useful, they are not without their disadvantages, a major disadvantage being in that they are either complicated in their construction and consequently are labor intensive in their manufacture and/or are expensive in their design and consequently are not particularly suited to be used as single-use, i.e., disposable devices. These and other shortcomings present in prior art devices also evidence the real and continuing need for improvements to electrically heated vapor dispensing apparatus. These and other shortcomings present in prior art devices have prompted the inventors to produce the present invention.

Accordingly, it is an object of the invention to provide an electrically heated vapor dispensing apparatus which is relatively simple in its construction, is effective in dispensing an amount of a volatile substance to an ambient environment such as the interior of a room, and due to its economic materials and method of construction, may be disposed of after one use.

It is a further object of the invention to provide an improved electrically heated vapor dispensing apparatus which may be used a plurality of times in conjunction with a replaceable volatile substance in a suitable container.

It is a yet further object of the invention to provide an improved method for the manufacture of an electrically heated vapor dispensing apparatus.

It is a still further object of the invention to provide a method for dispensing a volatile substance to an ambient environment such as a closed room or any other closed space which comprises the step of: providing an electrically heated vapor dispensing apparatus as described herein which is in electrical connection with a suitable power source.

These and other objects of the invention are satisfied by the present invention which is described in more detail below.

The electrically heated vapor dispensing apparatus according to the invention includes a base portion which is generally planar in structure having a top surface, and a bottom surface from which extends perpendicularly two (or more) suitably dimensioned electrical plugs. The base portion further includes incorporated within its construction a heating means which, when the electrical plugs are connected to a suitable electrical source, said heating means is energized, resulting in the heating of the base portion. Further, the base portion of the invention includes a radiator means which is in physical contact with the top surface of the base portion and preferably is coincident with substantially the entire top surface of the base portion such that the radiator means is a thin sheet or film layered and registered in contacting the top surface.

Figure 1:
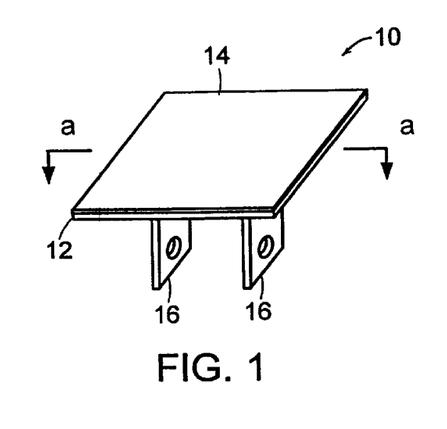
FIG. 1 shows a perspective view of a base portion of an electrically heated vapor dispensing apparatus according to the present invention.

Turning now to FIG. 1, there is depicted a base portion (10) according to a preferred embodiment of the present invention. The base portion includes a base (12) which has a top surface (not shown) which is substantially completely covered by the radiator means (14) which is layered in register and in physical contact therewith. The base portion further includes electrical plugs (16) which in the present and following figures illustrating the invention, are two spade type plugs which are in conventional use in North America. It is to be understood however that other configurations for suitable electrical plugs may be used for example those of circular cross section such as are in present use in Europe, three spade type plugs having the configuration in conventional use in the United Kingdom, as well as spade type plugs at a tilted or slanted angle as is in conventional use in Australia. The precise dimensions and configuration of these electrical plugs are not critical, but need only correspond to the dimensions required for the electrical wall receptacles into which the electrical vapor dispensing apparatus is intended to be connected to a suitable power source. Thus, by variation of these electrical plugs (16), the apparatus according to the present invention, may be readily adapted to be used virtually anywhere in the world.

With regard to the radiator means (14), said means is a heat conducting material and is preferably a thin plate, sheet, film, or tape which may be readily affixed to the top surface of the base portion and to substantially cover (which is to be understood as most, i.e., in excess of 75% of the of the area) of the top surface. Most desirably, the radiator means is a thin metal or metallic film or foil having a thickness of between about 0.01 to about 2 millimeters, and more preferably from about 0.1–1 millimeter. Such a plate, sheet, film, or tape may simply layered or stacked on top of the top surface of the base (12). Desirably, such a plate, sheet, film, or tape is directly applied to the top surface of the base (12) with the aid of a suitable adhesive material interposed between the radiator means (14) and the top surface of the base (12). Such an adhesive material is desirably present in an amount which is sufficient to provide proper adhesion between the top surface of the base and the radiator means. Further, desirably such an adhesive layer is not so thick as to substantially reduce the transfer of heat from the base to the radiator means. Desirably, the radiator means is a metallic plate, sheet, film or tape such one formed from on including iron, gold, silver, lead, chromium, aluminum, nickel, copper of virtually any other heat conducting metal including alloys which includes of one or more of the above such as brass, bronze, tin and zinc, as well as ferrous alloys, stainless steel, aluminum alloys and the like. Most desirably the radiator means (14) is tape or film having an adhesive deposited on one side which is then readily adherable to the top surface of the base (12).

Alternatively, the radiator means (14) may be a metallic material or a material which contains metallic particles other than those recited above which are applied to the top surface of the base (12). For example, radiator means (14) may be directly deposited by vapor deposition techniques, or may be a metallic material or metallic particle containing material which is applied by sputter-coating techniques, as well as mteallic particles contained within a coating composition which may be directly laid on the top surface, such as be screen printing techniques. In such a method, the coating composition may require subsequent drying or curing of said composition prior to the use of the apparatus according to the invention.

Figure 3:
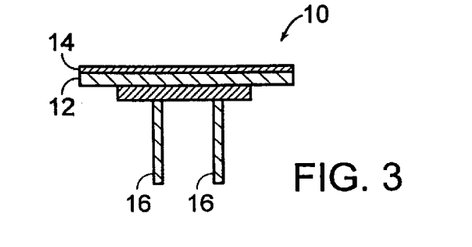
FIG. 3 illustrates a side view of the base portion of FIG. 1.

Turning now to FIG. 3, therein is depicted a side view of the base portion (10) according to FIG. 1. As is therein illustrated, the radiator means (14) is layered in register with the top surface (not shown) of the base (12). The base portion (10) further includes two electrical plugs (16) which extend perpendicularly from post portion (18) of the base (12) and a portion of each of the plugs (16) is are embedded within said post portion (18). It is to be understood that the post portion (18) depicted is an integral part of the base (12) and if the base (12) is of a sufficiently thick dimension to contain the heating means and provide a support for the plugs (160, the post portion (18) may be omitted from the construction of the base (12).

Figure 4:
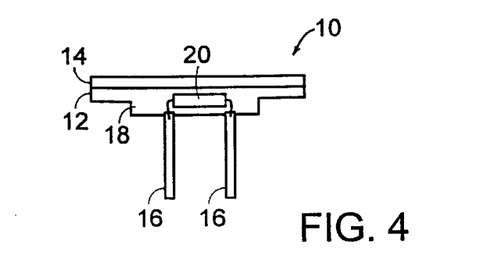
FIG. 4 illustrates a cut-away side view of the base portion according to FIG. 1 along reference line a—a, as well as according to FIG. 3.

With reference now to FIG. 4, therein is shown a cross-sectional view taken along line "a—a" of FIG. 1., as well as being similar to that depicted in FIG. 3. Illustrated in this cross-sectional view is a heating means (20) in electrical communication with each of the electrical plugs (16). The heating means (20) may be any electrical resistance device which, when connected to the power source such as available in a wall outlet, causes the generation of heat which is then dissipated into the base (12). A wide variety of known electrical devices may be used and generally any which includes a resistance element such as a bulb filament, a wire segment such as as of nichrome wire, but is most desirably an electrical resistor device as is commonly known in the electronic arts. It is required only that the heating means provide sufficient heat such that when dissipated into the base portion causes the volatilization of the volatile substance as will be described in more detail hereafter.

Figure 5:
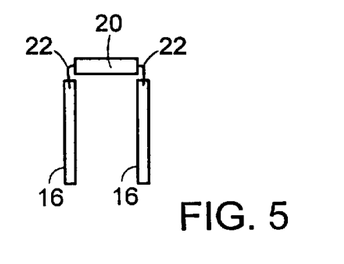
FIG. 5 illustrates a portion of the preferred heating means according to the present invention.

Turning now to FIG. 5, there is illustrated a side view of two plugs (16) and the preferred embodiment of the heating means (20), viz., an electrical resistor. With regard to the selection of the resistor, any which generates an appropriate amount of heat to induce the volatilization of the volatile material in the apparatus according to the present invention may be used, while at the same time does not undesirably soften or melt the material of which the base portion is formed. It is to be understood that the actual selection of such a suitable electrical resistor is in part dependent upon the power source to which it is to be attached, as well as on the characteristics of the vaporizable material with which it is to be used. By way of non-limiting example, for use with a 120 v, 50/60 cycle alternating circuit power source (such as in common use in North America) an electrical resistor especially an electronic resistor device rated from between 0.1 and 2 watts, and having a resistance in the range of from 1 to 100,000 ohms is generally appropriate for use. A specific preferred embodiment is described in the Example, below. The electrical resistor namely, an electronic resistor device includes two resistor leads, i.e., wires which extend from the resistor, and one of each wires (22) is in electrically conductive contact with a plug (16). While not illustrated in particular detail, it will be understood that any means for effecting such an electrically conductive contact may including but not limited to: a crimped or soldered connection between the wires (22) and the plugs (16) as well as wrapping or otherwise contacting a portion of the wires (22) with the plugs (16).

With regard to the base (12) as well as its integral post portion (18) (if present), such is desirably formed from a thermoplastic or thermosetting polymeric material which has sufficient heat tolerance such that it is not undesirably softened or melted when the heating means incorporated within is energized during normal use of the appratus. Such may be any of a variety of known materials which by way of example include polymers and/or copolymer resin compositions based on: nylons, polyethylene terephthalate, polybutylene terephthalate, polyolefins, styrenes, polyacetal resins, polysulfones, as well as others which exhibit such desired heat tolerance properties as denoted above. Such mateirials may be blends of one or more such polymers and/or copolymers, as well as commerically available polymeric compositions which may include additives or modifiers such as fillers including talc, comminuted carbons such as carbon black, glass fibers, glass beads, any of a variety of fire retardant materials, as well as colorants, pacifiers, pigments, and the like. The inclusion of one or more conventional additives to the polymer may be desired to adjust the properties thereof, such as to impart desirable physical properties such as stiffness, and/or heat transfer characteristics of the polymer material. Of such polymer and/or copolymer resin compositions, thermoplastic resins which may be used in an injection molding process are desirably used. An advantage of the use of such an injectable polymeric material is that in the manufacture of the base portion, the heating means and the plugs may be first preassembled, subsequently inserted into a suitable die cavity, and afterwards a quantity of the injectable polymer resin may be introduced into the die cavity to form the base in a single manufacturing step. In such a step, the plugs (16) may be positioned within the base (12), and at the same time the polymer resin composition envelops the heating means at all sides. Thereafter, the radiator means (14) may be applied in register with the top surface of the base (12) in order to form the base portion (10) according to the electrically heated dispensing apparatus within the scope of the present invention.

Figure 2:
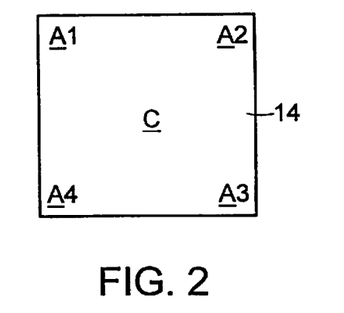
FIG. 2 depicts a top view of the base portion of FIG. 1.

A specific and surprising technical advantage of the construction of the base portion (10) according to the present invention includes the excellent and uniform heat distribution characteristics which are provided. With reference now to FIG. 2, therein is illustrated a top view of the base portion (10) according to FIG. 1. The top surface includes a radiator means and further depicted on FIG. 2 are further reference characters which indicate particular regions of the radiator means. More particularly, in FIG. 2, "A1" represents the region of a first corner, "A2 the region of a second corner, "A3" the region of a third corner, and "A4" the region of a fourth corner of the radiator means (14). Further, the letter "C" indicates the central region of the same radiator means (14). The present inventors have surprisingly found that when a base portion according to FIG. 1 was constructed, but without the use of a radiator means, that a wide and disparate variation in the temperatures observed at each of these indicated regions occurred. These results are illustrated on Table I below. The inventors have also surprisingly observed that a significant improvement in the temperature characteristics are provided by the base portion (10) according to the present invention than might be expected. Surprisingly, the present inventors have found that not only was the differential in temperature between the central region C and any of the corner regions A1, A2, A3 or A4 of the radiator means no more than a few degrees in temperature (celsius), which provided that the temperature gradient across the surface of the radiator means (14) was low, and was almost level as compared to the base portion without the radiator means (14). Further surprisingly, as compared to a similar base portion without the heat radiator means, the temperature of the central region C was significantly higher than when the radiator means (14) was included in the construction of the base portion (10). Such observations are more fully described in conjunction with the Example below. Generally, any of the corner regions were within 5° C. of the central region, and are more desirably within 3° C. of the central region of the radiator means (14) of the base portion (10) according to the invention.

Figure 6:
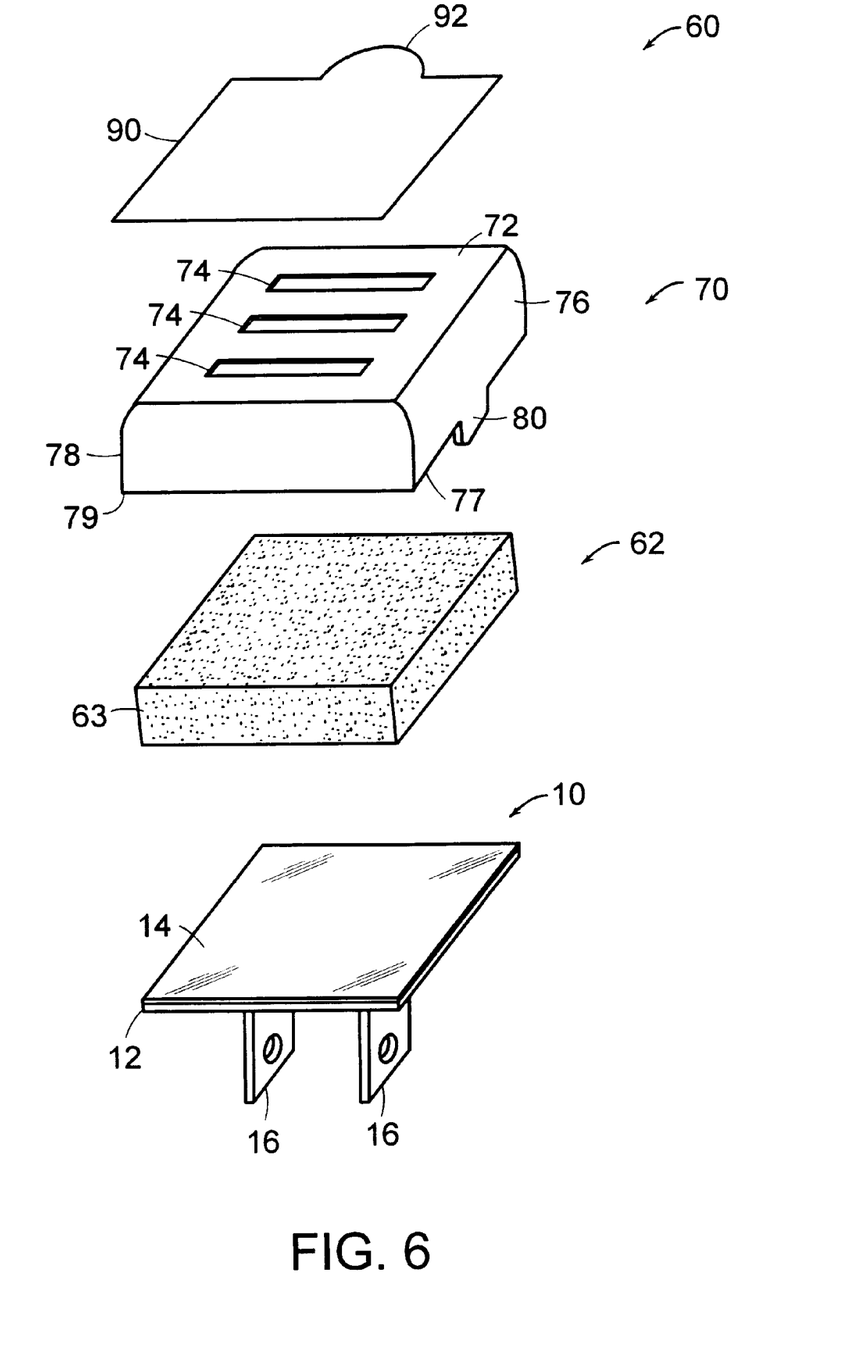
FIG. 6 illustrates an exploded perspective view of an electrically heated vapor dispensing apparatus according to a first preferred embodiment of the invention.

Turning now to FIG. 6 there is illustrated in an exploded view the elements which comprise a first preferred embodiment of an electrically heated vapor dispensing apparatus (60) according to the present invention. Therein is provided a base portion generally indicated as (10), which includes a base (12) having extending perpendicularly from a bottom surface thereof two plugs (16). On the opposite surface, the top surface, is a radiator means (14) layered in register with the top surface (not shown) of the base (12). Next (intended to be layered in register) is a volatile substance container (62) which contains a quantity of a volatile substance such as a fragrance or perfume, a disinfecting composition, or an insecticide. The next element which is included in this preferred embodiment is a shell generally referenced as (70), said shell (70) including a top wall (72) have a plurality of openings (74) passing therethrough. The shell (70) also includes two opposite side walls (76) and (78) (not shown) which have extending downwardly beyond their corresponding bottom edges (77), (79) a snap lock tab (80) which is suitably dimensioned to be engaged with at least a portion of the base (12) of the base portion (10) when the apparatus is assembled. The shell (70) is hollow in its interior and is suitably dimensioned to accommodate and completely confine the volatile substance container (62) within its interior when the shell (70) is affixed to the base (10). In this figure, the volatile substance container (62) is in the form of a porous container (63) which includes within a quantity of a vaporizable material as will be described in more detail below.

While optional, it may be further desired to include a cover film (90) which cover film may be any vapor impermeable or poorly vapor permeable material. The cover film itself may include an adhesive on one side thereof which is intended to cover and seal all of the openings (74) which may be when present in the shell (70). The cover film (90) itself may include a graspable portion thereof such as extended tab (92) illustrated on FIG. 6. The presence of such a tab, although not necessary, greatly facilitates the ability of an individual to grasp the cover film and remove it from the top wall (72) of the shell prior to the insertion of the apparatus into a wall outlet. While such a cover film is optional the inclusion of such a cover film is especially advantageous. The use of such a cover film (90) slows or halts the volatilization of the volatile substance from the interior of the apparatus and maintains the same in a ready-to-use condition for the ultimate consumer. The consumer of the product then needs only remove the cover film (90) and subsequently insert the plugs (16) into a suitable wall outlet which acts to connect them to a suitable power source.

With regard to the volatile substance (62) as illustrated in FIG. 6, therein is depicted one embodiment of such container which is in the form of a block (63) of a porous material. Preferably, such a porous material is a porous polymeric material such as a sintered polymer material which may be immersed, doused, or otherwise supplied with a quantity of a volatile substance such as a fragrance or perfume, disinfecting composition or insecticide which is entrained therein and when the porous material is heated to the temperatures provided by the base portion (10) of the apparatus according to the invention, induces the volatilization of the said volatile substance. Further preferably the porous material may be a porous ceramic material which may be any of a large class of nonmetallic, inorganic materials containing high proportions (i.e., at least 75% wt.) of silicon, silicon oxide, silicates as well as other materials not particularly elucidated here, and which have a porous structure which acts to absorb or entrain the volatile substance used. These include clays, porcelains, terra cotta, talc, cements as well as other ceramic materials which are known to the art which feature a porous structure. Such may be formed into a suitably dimensioned configuration, such as is described herein using conventional casting or molding techniques. It is further contemplated that none, all or part of the surface of such a block (63) constructed of a ceramic material may be glazed, coated or at least partially encased in an impermeable container.

It is yet a further embodiment a fibrous material which is porous and which may be used to entrain quantity of the volatile substance as described above may also be used as the volatile substance container (62) as depicted in FIG. 6. Non-limiting examples of such fibrous material may be of any construction, such as a block, pad or sponge of compressed, woven or non-woven fibrous material which may be inserted into the electrically heated vapor dispensing apparatus as described in FIG. 6. Exemplary fibrous materials include naturally occurring or synthetic fibrous materials as well as blends of two or more such fibrous materials. Advantageously, those based on naturally occurring or regenerated cellulose fibers in the form of compressed blocks may be utilized, with compressed sheet-like constructions especially to be preferred. Absorbent celluslose comprising paper pads or sheets are particularly advantageously used. Such cellulosic construction is desirably utilized as it is excellent in entraining a quantity of the volatile substance, may be easily and cheaply produced, and has little likelihood of ignition or charring when heated to an appropriate volatilization temperature.

Figure 7:
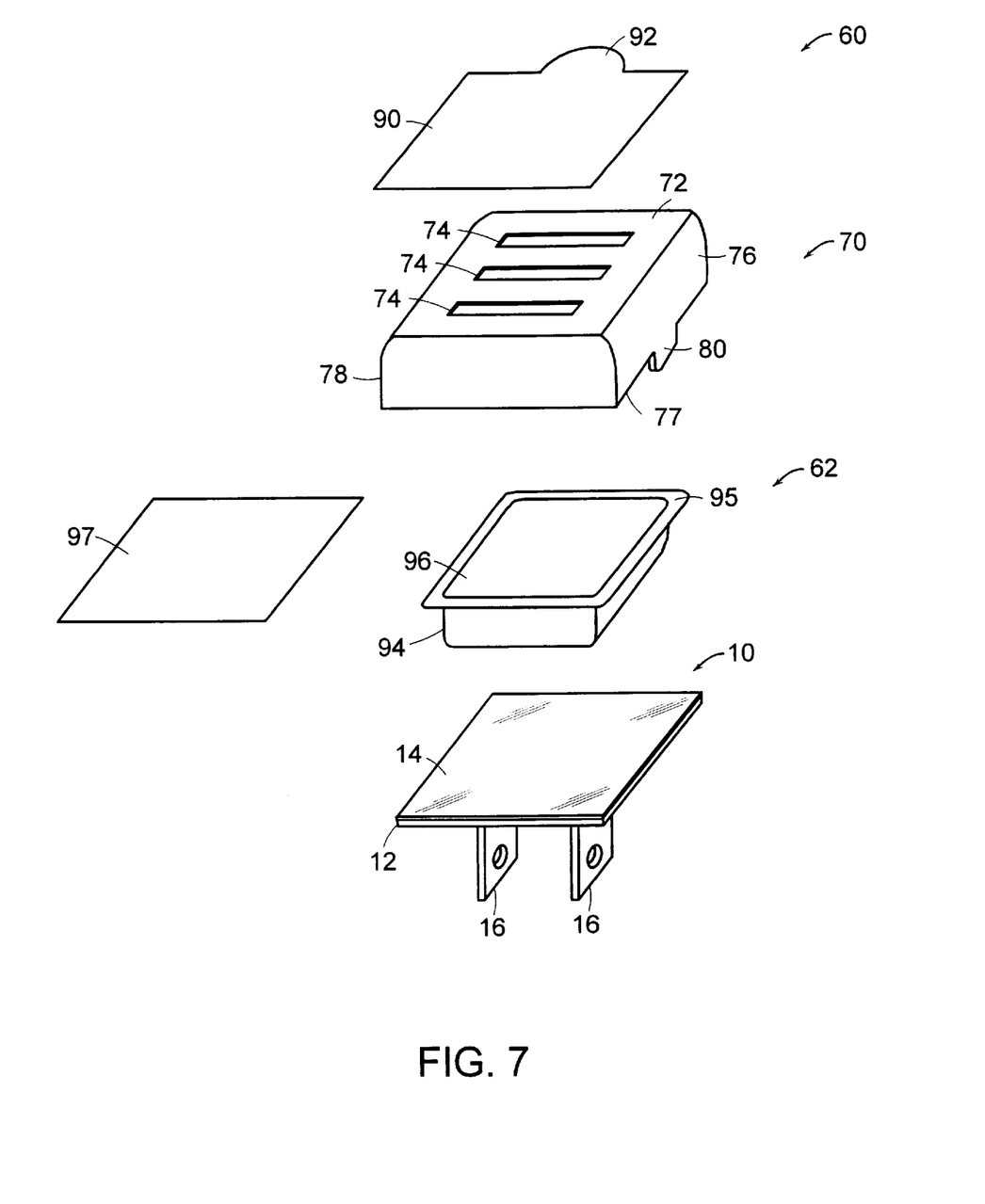
FIG. 7 illustrates an exploded perspective view of an electrically heated vapor dispensing apparatus according to a second preferred embodiment of the invention.

Turning now to FIG. 7 there is illustrated a second preferred embodiment of the electrically heated vapor dispensing apparatus (60) according to the present invention. The present apparatus is similar in most respects to the apparatus illustrated on FIG. 6 and corresponding elements are corespondingly numbered. In this second embodiment, the construction of the volatile substance container (62) differs from that previously described in FIG. 6. According to FIG. 7, the volatile substance container (62) comprises a container element (94) which has contained therein a quantity of a volatile substance composition (96), which may be in a liquid form, or in a solid, or semi-solid form such as a gell or paste-like form. The container element in (94) may be any housing of a configuration which is suited for the retention of the volatile substance composition (96) contained therein, is constructed of a material which is impermeable or only poorly permeable to said volatile substance composition (96) contained within, and which is suitably dimensioned to fit between the top surface of the base portion (10) and within the interior of the shell (70). Any variety of materials may be used in the construction of this container element (94) including, but not limited to, polymeric materials, metallic materials, as well as those formed from paper constructions such as paper coated on one or more surfaces with a material which resists the permeation of the volatile substance into the paper.

Turning now to the volatile substance composition (96) such may be solid, or semi-solid form such as a gel or paste-like form. By way of non-limiting example such compostions include a gelling agent which may be any of those known to the art such as fumed silica, DBS, carageenan as well as others not denoted here. The advantage of the utilization of such a volatile substance composition (96) is that generally, compared to other forms, such a composition provides ability to include therein a high proportion of the volatile substance intended to be delivered by the apparatus with respect to its base or carrier component. The volatile substance composition (96) may also be a porous substrate such as the porous ceramic or porous polymer material described in cojunction with the block (63) which contains a quantity of a volatile substance.

Desirably although not illustrated in FIG. 7, it is to be clearly understood that a single or bi-layered or multilayered film (97) may be provided to cover the volatile substance composition (96) within the volatile substance container (62). Such a film may be a single layer film, such as a vapor permeable membrane. Alternatively a single layer film which is vapor impermeable may be used, such as a film of a polymer exhibiting good vapor barrier properties or a metal film or foil. In such an embodiment, the vapor impermeable film is removed such as by peeling off from the volatile substance container (62) prior to the use of the apparatus. In a further alternative, the film may be a bi-layered or multilayered film which includes a vapor permeable membrane layer, and a vapor impermeable membrane layer. In such a construction, the vapor permeable membrane layer is layered between the volatile substance composition (96) and the vapor impermeable layer, and in use, desirably the vapor impermeable layer is removed such as by peeling off said layer and may be discarded. The vapor permeable membrane layer is retained as part of the volatile substance container (62) and covers the volatile substance composition (96) which may then be used in the apparatus according to the invention. Such single layer, bi-layer and multilayer films are known to the art and include those formed from polyolefins including for example polyethylene and polypropylene especially low density grades of such polyolefins; copolymers such as ethylvinylacetate copolymers, as well as other commercially available membrane materials including Teslin, silicone coated paper as well as Tyvek (DuPont, Wilmington Del.) may be useful as vapor permeable membrane, single layer, bi-layer and multilayer films are known to the art which are useful as vapor impermeable films include virtually any known to the art such as metal foils, polymeric films having a sufficiently high barrier property to the volatile material such as fluoropolymer contiaining films and PVDC. Methods for affixing such films to the volatile substance being suitably affixed such as by heat sealing, gluing, or other affixing via appropriate means to the container element (94). This may be facilitated by including a flange (95) which extends along the periphery of the container element (94). In this manner, when a vapor permeable membrane is provided such permits the volatile substance to pass from the container element (94) yet denying the passage of the volatile substance composition (96) contained therein to phycially flow out or fall out. Where there is provided a single or multi-layer, especially a bi-layered film having a vapor impermeable layer such as a metal foil or vapor impermeable polymer film, such a construction is particulary advantageous for use where the apparatus of the invention may be used a plurality of times. In such case, the volatile substance container (62) may be provided as a refill cartridge to a consumer, who need only remove the vapor impermable layer prior to inserting the volatile substance container (62) in contact with the base portion (10) of the apparatus according to the invention.

Figure 8:
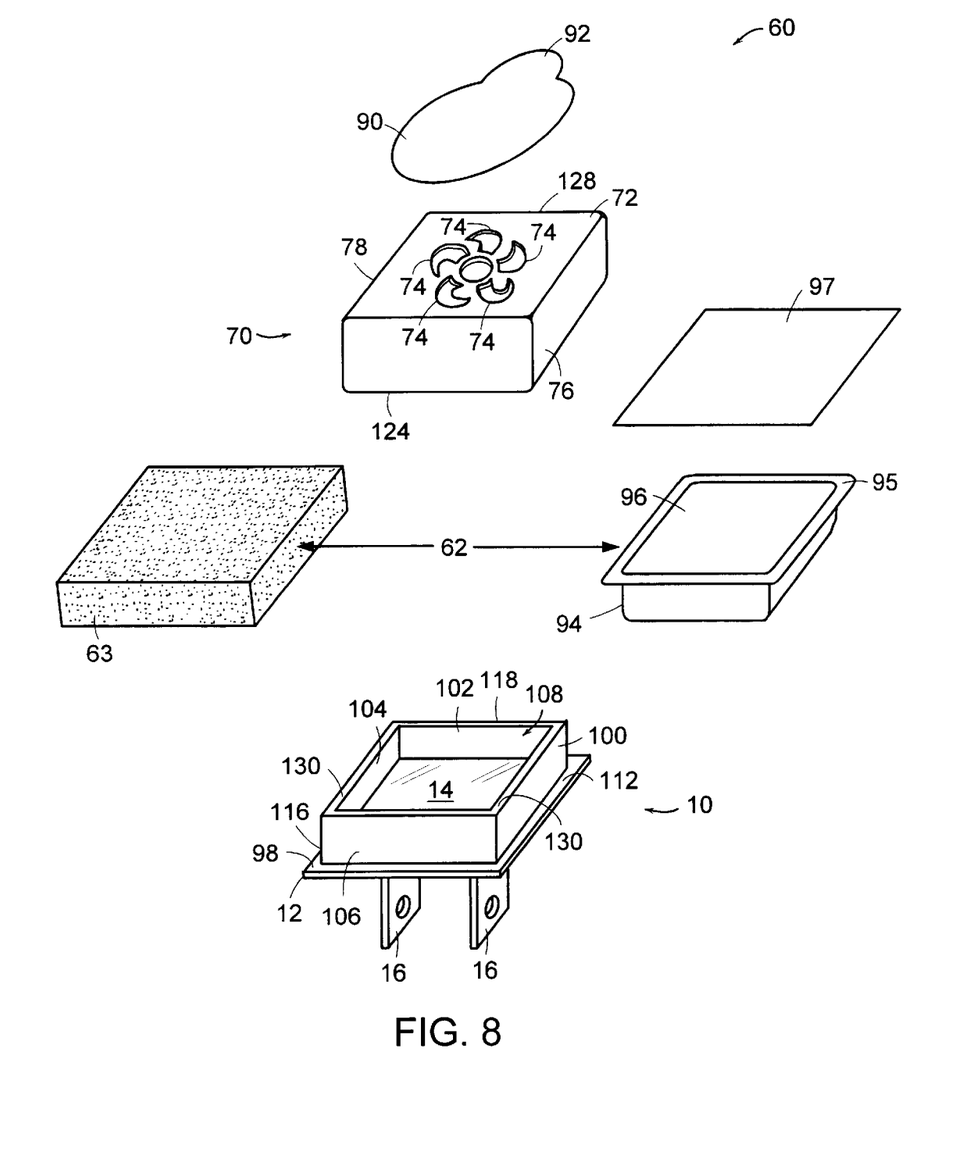
FIG. 8 illustrates an exploded perspective view of an electrically heated vapor dispensing apparatus according to a third preferred embodiment of the invention.

Turning now to FIG. 8 there is illustrated in perspective view the elements which may be used to construct a third preferred embodiment of the electrically heated vapor dispensing apparatus according to the invention, again generally indicated as (60). Therein as depicted, is included a base portion generally referred to as (10) which includes a base (12) having perpendicularly extending downwardly from bottom face thereof two plugs (16). The base portion further includes a top face (98) which has extending perpendicularly therefrom four walls (100), (102), (104), (106) which are generally rectangular in configuration and which are joined at corners, the said four walls defining a generally square enclosure (108) which extends from the top surface (98) of the base (12). Within the enclosure (108) and at top surface the base (12) thereof, is located the radiator means (14) here here illustrated as a metal foil which is adhered to the top surface within the confines of the enclosure. It is also to be noted that the dimensions of the walls are such that a marginal recess (112), (114) as well as (116), (118) (not visible), is present between the corresponding outermost edge of the base portion with the corresponding wall (100), (106) and although not visible shown in FIG. 8, such a recess exists at the base of each of the further walls (102), (104).

Further illustrated in FIG. 8 is an shell (70) having side walls (76), (78), (124) and (128) as well as a top wall (72). The top wall includes a plurality of openings (74) passing therethrough which are configured in the form of a decorative "flower petal" pattern which defines open passages between the interior of the shell (120) and the exterior, i.e., the ambient environment within which the electrically heated vapor dispensing apparatus is to be used. The shell (70) itself is dimensioned such that it may be slidably fitted upon the base portion (10) whereby the side walls (76), (124), (78) and (128) encase the walls (100), (106), (104) and (102) extending from the top surface (98) of the base (12). Desirably, these side walls (76), (124), (78) and (128) preferably rest in the recesses (112), (114), (116) and (118) (the latter of the two which are not shown). In this manner, either of the volatile substance containers (62) depicted and which have been described previously may be disposed within the enclosure (108) of the base portion (10) may be encased by the shell (70). Such volatile substance containers (62) may be either of the types as have been discussed with reference to FIG. 6 and FIG. 7.

The shell (70) and the base portion (10) may be interconnected by any suitable means, i.e., chemical means such as by disposing an adhesive material between portion of the shell (70) and the base portion (10) especially such as at the position of one or more of the recesses (112), (114), (116) and (118) of the base (10); by mechanical means such as by friction fitting, or as by providing snap-fitting elements such as described previously; or, by welding or melting, a portion of the shell (70) to bond it to the base portion (10).

Further, as has been noted previously, as it is contemplated that such an assembled electrically heated vapor dispensing apparatus (60) as is depicted in FIG. 8 may be expected to have a shelf life between its fabrication and the time of its use, such apparatus may also be provided with a cover film (90) which optionally includes a graspable tab (92) as has been discussed with reference to FIG. 6 and/or FIG. 7.

Figure 9:
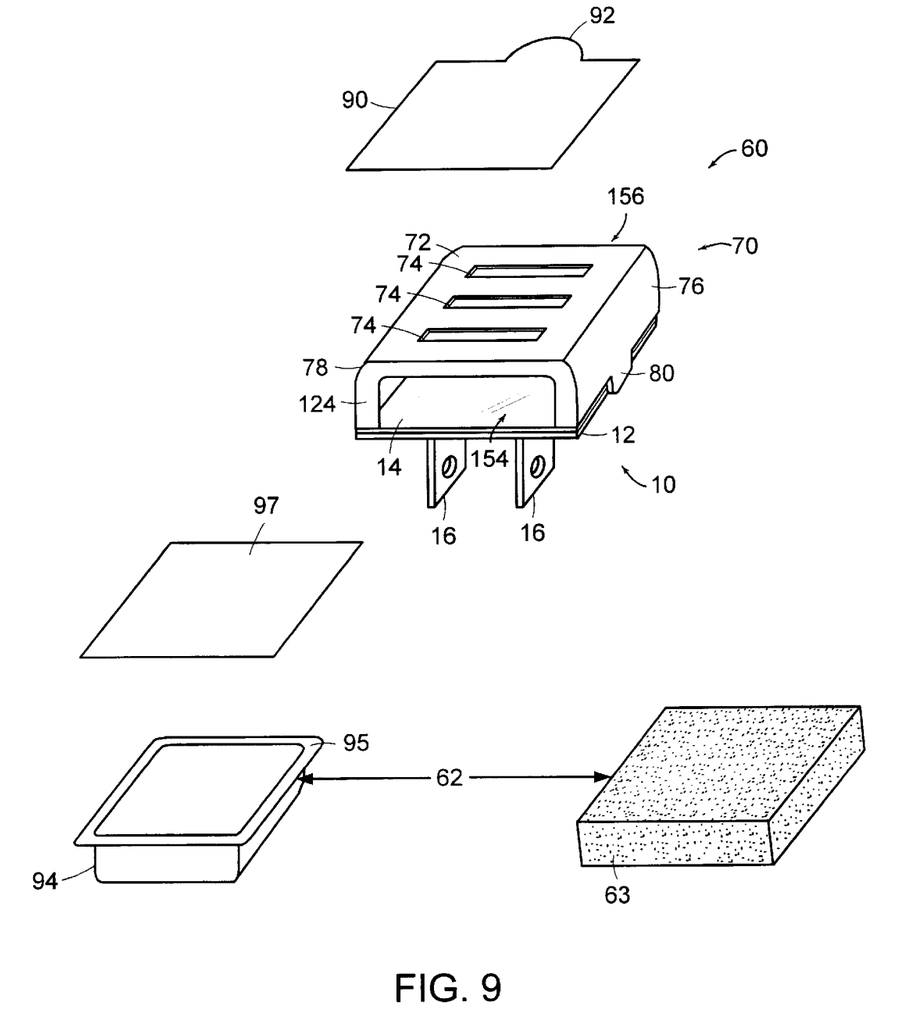
FIG. 9 illustrates an exploded perspective view of an electrically heated vapor dispensing apparatus according to a fourth preferred embodiment of the invention.

Turning now to FIG. 9 there is yet a further preferred embodiment of an electrically heated vapor dispensing apparatus (60) according to the present invention, in a partially assembled form. The apparatus according to the depicted embodiment is designed to be used a multiplicity of times as opposed to those more appropriate for a single use as disclosed and described in FIG. 1 through FIG. 8.

With regard to FIG. 9 therein depicted is a base portion (10) having a base (12) further including plugs (16) extending perpendicularly downwardly therefrom from a bottom surface, as well as a radiator means (14) disposed on the top surface (not shown) of the base (12). In this embodiment, the radiator means (14) is an aluminum foil tape or film which is adhered directly to the said top surface.

Further as shown, the shell (70) is mechanically engaged and "locked" to the base portion (10) by means of snap locking tabs (80), (81) (not shown) which grasps opposite edges of the base (10) and thereby engages and retains the shell (70) to the base portion (10).

The shell (70) includes at least one end wall (124) which includes an opening (154) therethrough to the interior of the shell (70) and such opening (154) is desirably a generally rectangular shaped opening (154) which is of sufficient size and suitably dimensioned to permit the insertion of either form of volatile substance container (62) as depicted and has been described in more detail with reference to earlier figures. Optionally such a volatile substance container (62) further includes a single or bi-layered or multi-layered film (97) which has also been previously described. Additionally, while not shown, the end wall (156) opposite to that of the end wall (124) having the opening therein (154) may be either solid, or may include a further opening therethrough to the interior of the shell (70). The embodiment according to FIG. 9 may also further include a cover film (90) which further includes a grasping tab portion (92) to facilitate its removal from the top wall (150) of the shell.

FIG. 9 illustrates a fourth particularly preferred embodiment of the electrically heated vapor dispensing apparatus according to the invention which is designed to be used a plurality of times. Namely, such an embodiment anticipates that once the volatile substance is dispensed from the volatile substance container (62) and that once emitted to a surrounding environment, the volatile substance container (62) may be readily removed and disposed of. Thereafter, the a further volatile substance container (62), of either type shown in FIG. 9 may be introduced into the apparatus (60) and the apparatus (60) thus reused. In such a manner, a yet further economy attendant upon the use of the apparatus according to the invention is possible, while retaining the beneficial volatile substance delivery characteristics as has been described previously in conjunction with the embodiments of FIG. 6–FIG. 8.

Figure 10:
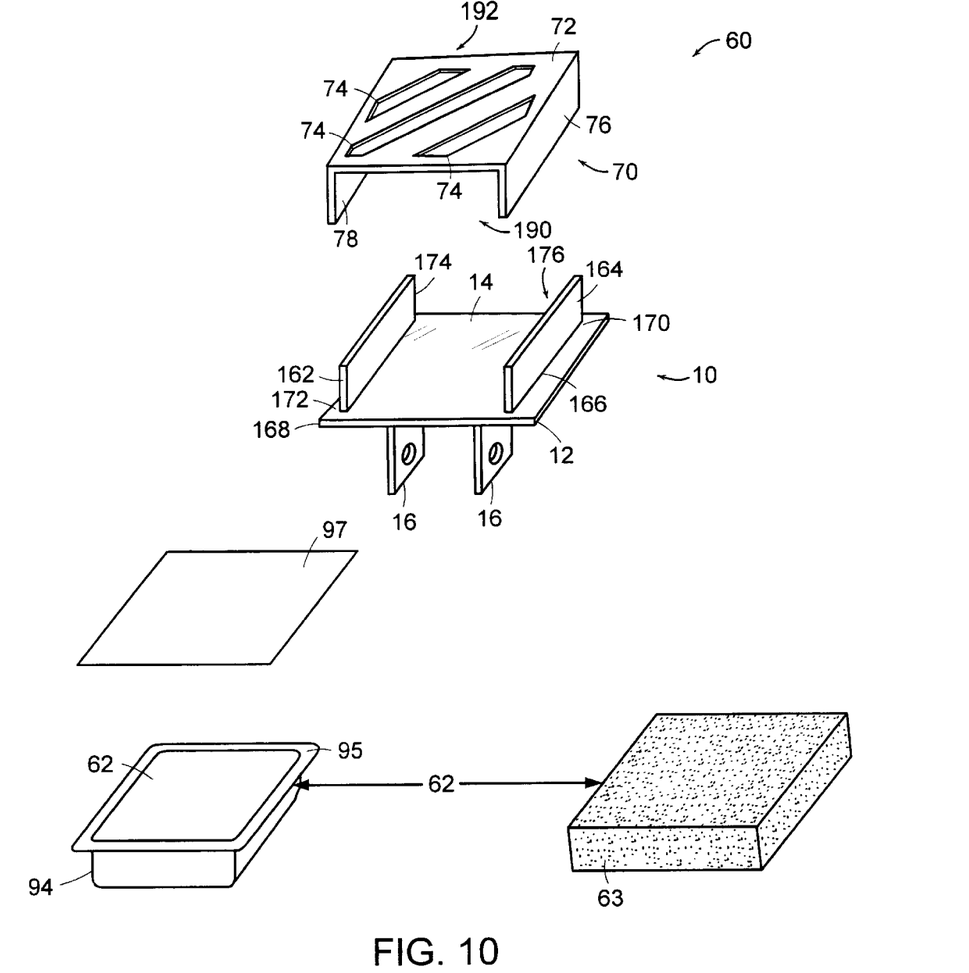
FIG. 10 illustrates an exploded perspective view of an electrically heated vapor dispensing apparatus according to a fifth preferred embodiment of the invention.

Turning now to FIG. 10 therein is disclosed a fifth preferred embodiment (60) according to the present invention which is one which may be used once or which may be used a plurality of times. The apparatus generally indicated as (60) includes a base portion (10) having a base (12) having two downwardly perpendicularly extending plugs (16) from a bottom surface, and a radiator means (14) disposed theron and covering substantially all of the top surface (not shown) of the base portion. Further extending upwardly substantially perpendicularly from the top surface of the base portion are two parallel walls (162), (164). The walls are positioned slightly inwardly from the corresponding edges (166), (168) of the base (12) so to define recesses (170), (172) between the base of each wall and their corresponding edge. Although not depicted in the figure, it is to be understood, however, that the walls (162), (164) may rise perpendicularly upwardly from the and be coincident with the edges (166), (168) of the base (12) in which case no such recesses (170), (172) would be present. Optionally, but in certain cases desirably, on the interior face of each of the walls (162), (164) is a longitudinally extending rib (174), (176) (not shown) which partially, or substantially along the complete width of the corresponding wall and parallel to the top surface of the base (12) and extends inwardly towards the opposite facing parallel wall. The function of these optional longitudinal ribs is to engage portions of a volatile container (62)which is intended to be inserted between the parallel walls (160), (162) when the apparatus (60) is used.

The apparatus (60) further includes a shell (70) having at least two side walls (76), (78) which are parallel to one another, and each of which are contiguous to opposite edges of the top wall (72). The top wall (78) further includes a plurality of passages (74) may be included passing through the top wall (72) of the shell (70). Such passages provide means for the volatilized volatile substance to escape into the ambient environment, although it is to be appreciated that the volatilized volatile substance may also escape at either of the open ends (190), (192) of the shell (70).

The electrically heated vapor dispensing apparatus according to the embodiment illustrated in FIG. 10 is formed by the combination of the shell (70) which is affixed to the base portion (10) in such a manner that the corresponding walls (76), (78) of the shell (70) are affixed to encompass corresponding parallel walls (164), (162) respectively of the base portion (10). Such affixing to one another by mechanical or chemical means as has been described above with reference to the embodiments discussed in the prior figures. Thereafter, either volatile substance container (62) depicted and also described previously is inserted into the interior of the apparatus (60) between the parallel walls (164), (162) where the longitudinal ribs (174), (176) when present, may facilitate their retention within the apparatus (60).

According to FIG. 10, a specific embodiment of an electrically heated vapor dispensing apparatus having a "slideway" is provided, wherein such an apparatus construction features a repeated use of the said apparatus prior to its disposal.

Figure 11:
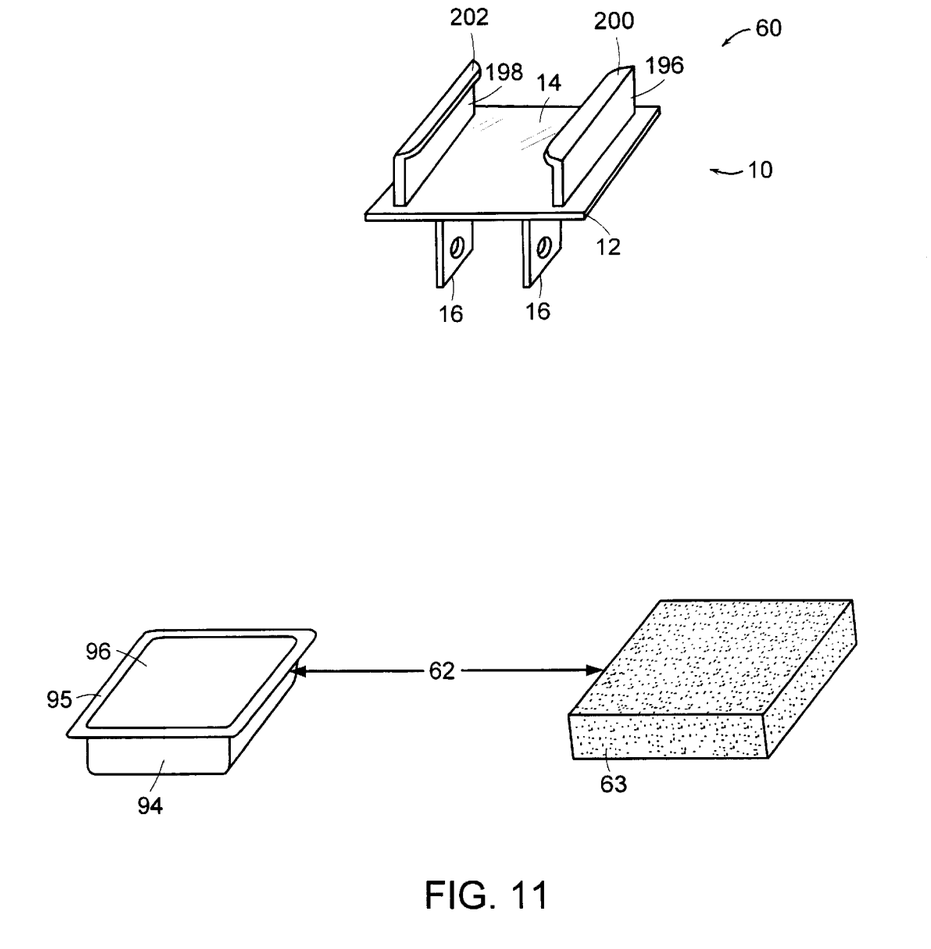
FIG. 11 illustrates an exploded perspective view of an electrically heated vapor dispensing apparatus according to a sixth preferred embodiment of the invention.

Turning now to FIG. 11 therein is illustrated in an exploded view the elements of a sixth preferred embodiment of the electrically heated vapor dispensing apparatus (60) according to the invention which does not include a shell.

As is shown on FIG. 11, the apparatus (60) includes a base portion (10) having a base (12) which includes plugs (16) extending perpendicularly from a bottom surface therefrom and radiator means (14) disposed on the face of the top surface. Further extending perpendicularly from the second face therefrom are two spaced apart walls (196), (198), each of which has a flange portion (200), (202) which desirably extends in the direction of the opposite wall, and most desirably is perpendicular to the wall from from which the flange extends. Further desirably, the each flange portion (200), (202) extends perpendicularly from the edge of the wall (196), (198) which is distal from the base (12), which is at a height above the base (12).

The electrically heated vapor dispensing apparatus according to this sixth preferred embodiment, may be assembled by inserting either of the volatile substance containers (62) as depicted on the figure, both of which have been described in detail previously. Either of these two elements may be slidably inserted and disposed between the radiator means (14), the walls (196), (198) and at least a portion of the respective flanges (200), (202). Such a slidably fittable assemblage may be readily produced with good tolerances of the respective corresponding elements.

Figure 12:
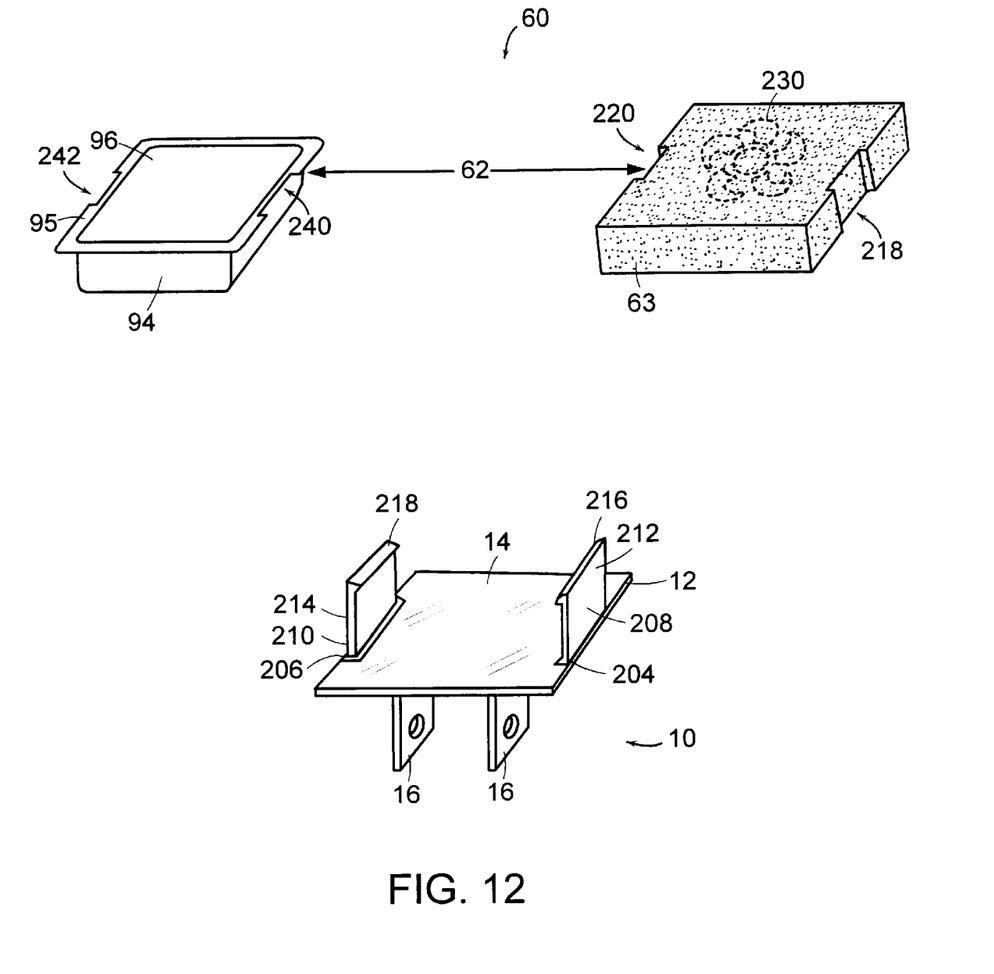
FIG. 12 illustrates an exploded perspective view of an electrically heated vapor dispensing apparatus according to a seventh preferred embodiment of the invention.

FIG. 12 illustrates a seventh preferred embodiment of the electrically heated vapor dispensing apparatus (240) according to the present invention.

Turning now with attention to the apparatus (60) depicted on FIG. 12, such an apparatus comprises the base portion (10) which includes the base (12) having perpendicularly extending plugs (16) extending from a bottom surface and a top surface upon which is disposed a radiator means (14). With specific attention to the embodiment illustrated on FIG. 12 it is to be noted that the radiator means (14) is in the form of a rigid metallic plate which is not necessarily adhered to the top surface (not shown) of the base (12), but rather includes recessed portions (204), (206) which are dimensioned to be fitted between the base portions (208), (210) of two upwardly extending side clip walls (212), (214) which extend from the base (12) in a generally perpendicular upwardly from the base (12). The distal ends of each of the side clip walls (212), (214) include integrally molded snap fit locking means (216), (218) which are suitably dimensioned to ultimately retain a correspondingy dimensioned volatile substance container (62) which may be inserted between the side clip walls (212), (214).

The apparatus (60) further includes a volatile substance container (62) which herein is depicted as a porous ceramic element or a porous polymeric element (63) containing a quantity of a volatile substance entrained within. The volatile substance container (62) is dimensioned to desirably include corresponding recesses (218), (220) which are dimensioned to permit the passage of the side clip walls (212), (214).

Alternatively, the apparatus (60) further includes a volatile substance container (62) which is herein depicted as a container element (94) which has contained therein a quantity of a volatile substance composition (96), which may be in a liquid form, or in a solid, or semi-solid form such as a gell or paste-like form. Such has been described previously, particularly in conduction with FIG. 7. This volatile substance container (62) is dimensioned to desirably include corresponding recesses (240), (242) within the flange (95) which are dimensioned to permit the passage of the side clip walls (212), (214).

The electrically heated vapor dispensing apparatus (60) according to the seventh preferred embodiment is readily produced by merely physically inserting the volatile substance container (62) between the side clip walls (212), (214) until the container (62) is fully seated therein, and thereby permitting the snap lock elements (250), (252) to engage and to retain the volatile substance container (62) in a "locked" position. Such an arrangement also insures that the radiator means (14) is retained in the position intermediate and in physical contact with the base (12) and the volatile substance container (62). Advantageously, the volatile substance container (62) includes recesses (218), (220) which facilitate assembling the apparatus (60).

Although the embodiment of the apparatus (60) according to FIG. 12 is most useful as a single-use device, i.e., as disposal after the volatile substance is volatilized from within the volatile substance container (62), it is anticipated that the said container may be removed by disengaging the snap lock elements (250), (252), removing the volatile substance container (62) and replacing it with a further container having a quantity of volatile substance therein.

It is also to be understood that a raised or embossed, as well as a printed decorative design (230) may be included as part of the volatile substance container (62) so to improve the attractiveness thereof.

It is to be understood that the volatile substances which may be dispensed utilizing the apparatus described herein specifically includes insect repellent compositions, deodorizing compositions, medicinal compounds, herbal compositions as well as disinfectant compositions Especially preferred as volatilizable materials are those which emanate a fragrance or scent when volatilized, and are generally scented oils or perfumes which may be a pure essence oil or which may be a mixture of constituents such as a minor amount of a perfume or pure essence oil diluted in a greater volume of a volatile liquid base such as an alcohol. Many such materials are known to the art, and although not specifically described here, may be used and are to be particularly considered within the scope of the present invention.

As will be realized by a reading of the foregoing specification, the electrically heated vapor dispensing apparatus according to the present invention provides substantial contribution to the art in providing an apparatus which is inexpensive to make, may be economically disposed of, even after one use, but may also be reused a plurality of times and which due to its elegant and simple design, is reliable in its operation. Further, the apparatus according to the present invention has overcome many of the inherent shortcomings in the art, namely the effective distribution of heat and in the reliable, long-term, uniform volatilization of a volatile substance which is contained within such an apparatus whereby at a low power consumption required for its operation, a uniform and stable delivery rate of the volatile substance may be provided over nearly the complete life cycle of such a product. Further, the apparatus ensures that the volatile substance, whether encapsulated in a gel, gel-like, semi-solid, pasty carrier and/or in one of the porous materials, i.e., porous polymer and/or ceramic, is safely and uniformly delivered to an ambient environment such as the interior of the room or other closed volume of space.

EXAMPLE

A base portion (10) similar as depicted on FIGS. 1–4 was manufactured. The base portion (10) comprised a 1000 ohm resistor having a power rating of ¼ watt, with the first end thereof connected via a first resistor lead wire to a first plug and the other end thereof similarly connected via the other lead wire. The ends of these wires were crimped to the ends of the plugs. Subseqently the thus assembled resistor and plugs were inserted into a suitably dimensioned die cavity and an amount of polypropylene was injected therein. The thus formed base was ejected from the die cavity. The top surface of the base was 1⅜ inch by 1⅜ inch. The thickness of the top surface was ⅛th inch, and the bottom surface included a centrally located post portion having a thickness of ⅛th inch, a width of 1 inch and a length of ¾ inch. The resistor and the base portions of the two spade-type plugs were fully embedded in the base portion and/or the post portion.

The base thus produced was then inserted into a wall outlet of the type conventionally found in North America, which provided 120v alternating current, 50/60 cycles operation for at least 5 minutes, or until steady state heating of the base occurred. Temperature reading were taken using a surface temperature probe at the central region, and in each of the the regions of the four corners as is illustrated on FIG. 2. These results are reported on Table I, below.

Subsequently, the base was removed from the outlet, cooled and a piece of an aluminum foil tape was adhered to and covered substantially all of the top surface of the base. Again, this base according to the invention was then inserted into a wall outlet of the type conventionally found in North America, which provided 120v alternating current, 50/60 cycles operation for at least 5 minutes, or until steady state heating of the base occurred. Temperature reading were taken using a temperature probe at the central region, and in each of the the regions of the four corners as is illustrated on FIG. 2. These results are reported on Table I, below.

TABLE I

| region of base: | temperature of base | temperature of base according to invention |
|---|---|---|
| C | 91.67° C. | 58.33° C. |
| A1 | 61.67° C. | 57.22° C. |
| A2 | 45.56° C. | 56.67° C. |
| A3 | 52.22° C. | 57.78° C. |
| A4 | 57.22° C. | 56.11° C. |

While the invention is susceptible of various modifications and alternative forms, it is to be understood that specific embodiments thereof have been shown by way of example in the drawings which are not intended to limit the invention to the particular forms disclosed; on the contrary the intention is to cover all modifications, equivalents and alternatives falling within the scope and spirit of the invention as expressed in the appended claims.

What is claimed is:

1. An electrically heated apparatus for dispensing fragrancing materials and other volatile substances to an enclosed volume comprising:

a base having a base portion which is generally planar in structure having a top surface, and a bottom surface from which extends perpendicularly two or more electrical plugs, an electronic resistor device incorporated within the base portion, the electronic resistor device having two leads, a first least in electrically conductive contact with a first of the electrical plugs, and a second lead in electrically conductive contact with a second of the electrical plugs;

a radiator having a top surface and a bottom surface, the bottom surface which is layered in registered with the top surface of the base portion; and, a container element which contains a quantity of a volatile substance, layered in register with the top surface of the radiator.

2. The apparatus according to claim 1 wherein the radiator is a metal plate, foil or film.

3. The apparatus according to claim 1 wherein the volatile substance is in a liquid form, in a solid, or in a semi-solid, or paste-like form.

4. The apparatus according to claim 1 wherein the container element is a block of a porous material.

5. The apparatus according to claim 4 wherein the porous material is a porous polymeric material.

6. The apparatus according to claim 4 wherein the porous material is a porous ceramic material.

7. The apparatus according to claim 6 wherein the porous ceramic material is selected from nonmetallic, inorganic materials containing high proportions of silicon, silicon oxide, or silicates.

8. The apparatus according to claim 6 wherein the porous ceramic material selected from clays, porcelains, terra cotta, talc, and cements.

9. The apparatus according to claim 1 wherein the container element is a porous, fibrous material.

10. The apparatus according to claim 1 wherein the container element includes a volatile substance selected from the group consisting of fragrances, perfumes, disinfecting compositions, and insecticides.

11. The apparatus according to claim 1 which further includes a shell adapted to completely confine the container element.

12. The apparatus according to claim 11 wherein the shell includes one or more passages passing therethrough.

13. The apparatus according to claim 1 wherein the electronic resistor device is rated from between 0.1 and 2.0 watts, and has a resistance in the range of from 1 to 100,000 Ohms.

14. The apparatus according to claim 1 wherein the base is formed of a polymeric material and the electronic resistor device is wholly encased within the base portion.

15. A process for delivering a volatile substance to an enclosed volume which comprises the process steps of:

(a) providing an electrically heated apparatus for dispensing fragrancing materials and other volatile substances to an enclosed volume comprising;

a base having a base portion which is generally planar in structure having a top surface, and a bottom surface from which extends perpendicularly two or more electrical plugs, an electronic resistor device incorporated within the base portion, the electronic resistor device having two leads, a first least in electrically conductive contact with a first of the electrical plugs, and a second lead in electrically conductive contact with a second of the electrical plugs;

a radiator having a top surface and a bottom surface, the bottom surface which is layered in registered with the top surface of the base portion; and, a container element which contains a quantity of a volatile substance, layered in register with the top surface of the radiator, (b) connecting the electrical plugs into an electrical wall outlet within the enclosed volume and thereby heating the electronic resistor device and volatilizing the fragrancing materials or volatile substance.

* * * * *